(12) United States Patent
Bartke et al.

(10) Patent No.: US 7,282,482 B2
(45) Date of Patent: Oct. 16, 2007

(54) NGF FOR THE PREVENTION OF DEMYELINATION IN THE NERVOUS SYSTEM

(75) Inventors: Ilse Bartke, Mannheim (DE); Jurgen Unger, Landshut (DE); Claude Genain, Mill Valley, CA (US); Stephen Hauser, Ross, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/854,142

(22) Filed: May 10, 2001

(65) Prior Publication Data

US 2003/0032589 A1 Feb. 13, 2003

Related U.S. Application Data

(63) Continuation-in-part of application No. 09/529,369, filed as application No. PCT/EP98/02029 on Apr. 8, 1998.

(51) Int. Cl.
*A61K 38/18* (2006.01)

(52) U.S. Cl. .............................................. 514/12; 514/2
(58) Field of Classification Search .................. 514/12, 514/2
See application file for complete search history.

(56) References Cited

U.S. PATENT DOCUMENTS

| | | | |
|---|---|---|---|
| 5,210,185 A | | 5/1993 | Della Valle et al. |
| 5,904,144 A | * | 5/1999 | Hammang et al. .......... 128/898 |
| 5,935,577 A | * | 8/1999 | Weiner et al. ............ 424/184.1 |
| 6,268,340 B1 | * | 7/2001 | Unger et al. ................... 514/12 |

FOREIGN PATENT DOCUMENTS

| | | | |
|---|---|---|---|
| EP | 731108 A1 | * | 9/1996 |
| WO | WO 9303140 A1 | * | 2/1993 |
| WO | WO 97/17087 | | 5/1997 |
| WO | WO 9846254 A1 | * | 10/1998 |

OTHER PUBLICATIONS

Diaz–Villoslada et al. (Mar., 1997) Neurology, 48(3) Supp. [2], "Recombinant Human Nerve Growth Factor Prevents Autoimmune Demyelination in Marmosets", p. 15001, Abstract 142–143.*
Diaz–Villoslada et al. (Oct. 13–16, 1996) American Neurology Association Meeting, Miami, FL, USA, "Recombinant Human Nerve Growth Factor Prevents Autoimmune Demyelination in Marmosets".*
Unger et al., Poster presented at the Annual Meeting of the Society for Neuroscience, San Diego, California, Nov. 11–16, 1995, "Time course of regeneration in the adult pig brain following lysolecithin–induced demyelination".*
Angeletti and Bradshaw, (1970) *Proc. Natl. Acad. Sci. USA* 68:2417–2421.
Kandel et al., (1991) *Principles of Neural Science*, $3^{rd}$ Edition, Elsevier, p. 22.
Vinken, B., (1970) *Handbook of Clinical Neurology* 7, Diseases of Nerves, Part I, Chapter 19, pp. 495 et seq.
Althaus, et al., (1992) *Neuroscience Letters* 135:219–223, "Nerve growth factor induces proliferation and enhances fiber regeneration in oligodentrocytes isolated from adult pig brain".
Gage, et al., (1988) *The Journal of Comparative Neurology*, 269:147–155, "Morphological respnse of axotomized septal neurons to nerve growth factor".
Hefti et al, (1984) *Brain Research* 293:305–311, "Chronic intraventricular injections of nerve growth factor elevate hippocampal choline acetyltransferase activity in adult rats with partial septo–hippocampal lesions".
Hefti, (1986) *The Journal of Neuroscience*, vol. 6, No. 8, p. 2155–2162, "Nerve growth factor promotes survival of septal cholinergic neurons after fimbrial transections".
Crain and Patterson, (1974) *Brain Research*, 79:145–152, "Enhanced afferent synaptic functions in fetal mouse spinal cord–sensory ganglion explants following NGF–induced ganglion hypertrophy".
Chun and Patterson, (1977) *The Journal of Cell Biology*, vol. 75, pp. 596–704, "Role of nerve growth factor in the development of rat sympathetic neurons in vitro—I. Survival, growth and differentiation of catecholomine production".
Chun and Patterson, (1977) *The Journal of Cell Biology*, vol. 75, pp. 704–711, "Role of nerve growth factor in the development of rat sympathetic neurons in vitro—II. Developmental studies".
Levi–Montalcini and Angeletti, (1963) *Developmental Biology*, 7:653–659, "Essential role of the nerve growth factor in the survival and maintenance of dissociated sensory and sympathetic embryonic nerve cells in vitro".
Massacesi, et al., (1995) *Annals of Neurology*, vol. 37, No. 4, pp. 519–530, "Active and passively induced experimental autoimmune encephalomyelitis in common marmosets: A new model for muliple sclerosis".

(Continued)

*Primary Examiner*—Leon B. Lankford, Jr.
*Assistant Examiner*—Susan Hanley
(74) *Attorney, Agent, or Firm*—Quine I.P. Law Group, PC.; Paul Littlepage

(57) ABSTRACT

This invention pertains to the discovery that nerve growth factor (NGF) is capable of preventing further demyelination of nervous tissue in pathologies characterized by the demyelination of nervous tissue (e.g. multiple sclerosis). In one embodiment, this invention provides a method for inhibiting demyelination in a subject having an inflammatory disease of a nervous tissue. The method involves administering an effective amount of NGF, an NGF analogue, or an active fragment of NGF where the effective amount is sufficient to downregulate the production of interferon $\lambda$ by T cells infiltrating the central nervous system and/or to upregulate IL-10 production by glial cells.

14 Claims, 9 Drawing Sheets

OTHER PUBLICATIONS

Althaus et al., (1990) *Cellular and Molecular Biology of Myelination*, Monastery Ohrbeck, FRG, Aug. 28–Sep. 2, 1989; NATO ASI Series, vol. H43, edited by G. Jeserich et al., Springer Verlag Berlin Heidelberg 1990; pp. 247–253 "Protein kinases A and C are involved in oligodentroglial process formation".

Engel et al., (1994) NeuroReport 5:397–400, "NGF increases $[Ca^{2+}]_i$ in regenerating mature oligodendrolial cells".

Althaus and Siepl, (1997) *Cell Tissue Res.* 287:135–141, "Oligodendrocytes isolated from adult pig brain synthesise and release prostaglandins".

Diaz–Cintra, et al., (1995) *Cell Transplantation*, vol. 4, No. 5, pp. 505–513, "Morphometric study of fetal brain transplants in the insular cortex and NGF effects on neuronal and glial development".

Schmidt–Schulz and Althaus, (1994) *Journal of Neurochemistry*, 62:1478–1585, "Monogalactosyl diglyceride, a marker for myelination. Activates oligodendroglial protein kinase C".

Cohen, et al., (1996) *The Journal of Neuroscience*, vol. 16, No. 20, pp. 6433–6442, "Nerve growth factor and neurotrophin–3 differentially regulate the proliferation and survival of developing rat brain oligodendrocytes".

Miller, et al., (1996) *Brain Pathology* 6:331–34, "Central nervous system remyelination—clinical application of basic neuroscience principles".

Koliatsos, et al., (1990) *The Journal of Neuroscience* 10(12):3801–3813, "Mouse nerve growth factor prevents degeneration of axotomized basal forebrain cholinergic neurons in the monkey".

McMorris and McKinnon, (1996) *Brain Pathology*, 6:313–329 "Regulation of oligo dendrocyte development and CNS myelination by growth factors: prospects for therapy of demyelinating disease".

Kramer, et al., (1995) *Nature Medicine*, vol. 1, No. 11:1162–1166, "Gene transfer through the blood–nerve barrier: NGF–engineered neuritogenic T lymphocytes attenuate experimental autoimmune neritis".

The Merck Manual of Diagnosis and Therapy: General Medicine. Berkow, ed. vol. 1. 15th edition. (1987) (Merck Sharpe & Dohme Research Laboratories: Rahway, NJ) p. 1091.*

Awatsuji et al. (1993) Interleukin–4 and –5 as modulators of nerve growth factor synthesis/secretion in astrocytes. J. Neurosci. Res. 34:539–545.

Laudiero, et al. (1992) Multiple sclerosis patients express increased levels of beta–nerve growth factor in cerebrospinal fluid. Neurosci. Lett. 147:9–12.

Longo, et al. (1992) Nerve growth factor: actions in the peripheral and central nervous systems. In Fallon J., Loughlin S., eds. Neurotrophic Factors. New York, Academic Press, 209–256.

Webster (1997) Growth factors and myelin regeneration in multiple sclerosis. Mult. Scler. 3:113–120.

* cited by examiner

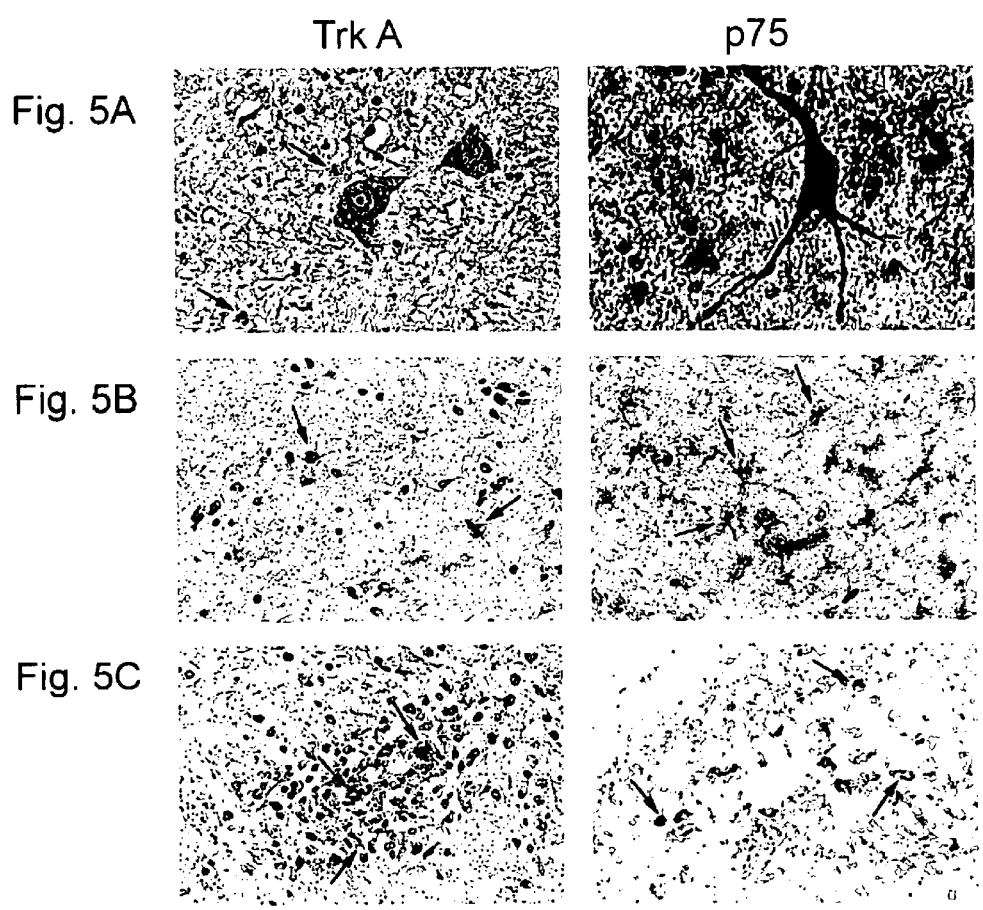

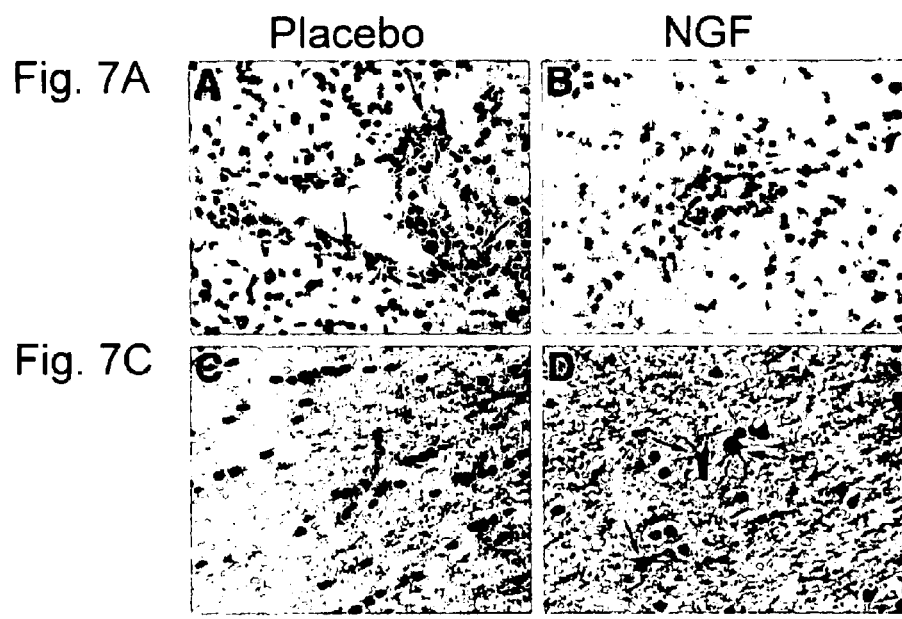

NGF FOR THE PREVENTION OF DEMYELINATION IN THE NERVOUS SYSTEM

CROSS-REFERENCE TO RELATED APPLICATIONS

This is a continuation-in-part of U.S. Ser. No. 09/529,369, filed on Jun. 8, 2001 which is a 371 filing of PCT/EP98/0202, filed Apr. 8, 1998, which claims priority to U.S. Ser. No. 08/833,959, filed Apr. 11, 1997, now abandoned all of which are incorporated herein by reference in their entirety for all purposes.

DETAILED DESCRIPTION

The present invention concerns a process for prevention of demyelination in the nervous system by administering NGF. In addition, the invention concerns a pharmaceutical composition for treating diseases in which a demyelination of nerve fibers occurs as well as a process for its production.

The covering of nerve fibers in the nervous system (NS) with myelin is essential for the function of neuronal signal transmission. The myelin sheath is formed by oligodendrocytes (OL) in central nervous system (CNS) cells or Schwann cells which wrap these myelin sheaths around the axon of a nerve cell. Oligodendrocytes are part of a separate non-neuronal cell population distributed throughout the CNS as part of the neuroglia. These are cells that are essential for the regular function of neurons, in the case of oligodendrocytes by forming the myelin sheaths around the axons, thereby increasing electric conduction of nerve impulses (Kandel et al., Principles of Neural Science, 3rd Ed., Elsevier 1991, p. 22). Therefore the identification and characterization of factors which are responsible for preventing the demyelination is very important for the molecular understanding of demyelinating diseases and for the development of therapeutic agents.

It is well known that NGF acts on different subtypes of neuronal cells. In the periphery NGF is a survival factor for sensory and sympathetic neurons (Levi-Montalcini, R. and Angeletti, P. U. (1963) Dev. Biol. 7: 653–659; Chun, L. L. Y. and P. H. Patterson (1977) J. Cell Biol. 75: 694–704; Chun, L. L. Y. and P. H. Patterson (1977) J. Cell Biol. 75: 705–711; Crain, S. M. and E. R. Peterson (1974) Brain Res. 79: 145–152.), in the central nervous system NGF is a survival factor for cholinergic neurons and prevents the degeneration of cholinergic neurons in the basal forebrain (Gage et al. (1988) J. Comp. Neurol. 269: 147–155; Hefli et al. (1986) J. Neurosci. 6: 2155–2162; Hefti et al. (1986) J. Brain Res. 293: 305–311.).

With the results of Althaus et al. a new characteristic of NGF was identified (Althaus et al. (1992) Neurosci. Lett. 135: 219–223, and International Application No. WO 93/03140). NGF induced proliferation and differentiation of oligodendrocytes, a non-neuronal cell population. These oligodendrocytes are specialized and the only cells in the central nervous system which are capable of producing myelin and wrapping the myelin sheaths around the axons. The oligodendrocytes and myelin sheaths are susceptible to attack by auto-immune processes, e.g., multiple sclerosis. Therefore, Althaus indicates that the induction of remyelination could be an important step in a therapeutic approach for multiple sclerosis.

In the present invention, another new characteristic of NGF has been discovered. NGF is able to prevent demyelination of nerve fibers of the nervous system of a mammal, preferably of a human being, by influencing the immune system or the blood brain barrier (endothelial cells, T cells, macrophages, monocytes and microglia cells) At the moment the mechanism by which NGF is effective is not yet clear. But prevention of demyelination is a new and unexpected activity of NGF. Preferably, the effective amount of NGF or active NGF fragments is between 10 and 300 pg NGF/ml CSF (cerebrospinal fluid).

Koliatsos et al. discloses that NGF prevents the degeneration of cholinergic neurons in the basal forebrain. This finding is exclusively focused on NGF-sensitive nerve cells (neurons) in a small area of the brain, whereas the present invention is directed to the prevention of demyelination throughout the brain.

This approach is completely unrelated to the known effect of NGF on cholinergic neurons or other neuronal populations.

The object according to the present invention is achieved by a process for preventing the demyelination of nerve fibers in the nervous system of a human being, wherein said human being is treated with an amount of nerve growth factor (NGF) or active fragments of NGF elective to prevent demyelination.

L. Massacesi et al. have developed and extensively characterized a novel model of experimental allergic encephalomyelitis (EAE) in a small non-human primate (Massacesi, L. et al., Ann. Neurol. 37 (1995) 518–530). In contrast to most forms of acute EAE in rodents and in other non-human primates, EAE in the common marmoset *Callithrix jacchus* (*C. jacchus*) is a clinically mild, relapsing remitting disease characterized pathologically by early and prominent demyelination with astrogliosis that is highly reminiscent of human multiple sclerosis (MS). Thus, this unique laboratory model is most suitable for testing substances which are useful for the prevention of demyelination.

The early studies had the limited objective of exploring the feasibility of such treatment in an animal model that closely resembled human MS. In testing the present invention, acute demyelinating EAE was induced in marmosets by active immunization with 100 μg recombinant rat myelin/oligodendrocyte glycoprotein (MOG) in adjuvant. Beginning 7 days after immunization, animals were treated with NGF or placebo (6 μg/day) administered intracerebroventricularly by continuous infusion. Animals were monitored in a blinded fashion for clinical signs of EAE cerebrospinal fluid (CSF) pleocytosis (e.g., inflammation), and immune cellular and antibody responses, for a period of 28 days following immunization.

In the NGF-treated animals, clinical EAE was delayed and markedly suppressed in severity compared to the controls. Neuropathologic examination of the NGF-treated animals corroborated the observation of clinical protection; fewer and smaller perivascular inflammatory infiltrates accompanied only by minimal demyelination were seen in the treated animals. This was in contrast with the large perivascular foci of inflammation with extensive demyelination which are usually present at the acute phase of MOG-induced EAE and which were also observed in the control animals of this study. Surprisingly, the results have uncovered an unforeseen effect of NGF, namely protection against EAE. This effect could be mediated by interaction of NGF with the immune system of the periphery or via local mechanisms within the central nervous system, possibly suppression of inflammatory mediators such as cytokines or leukotrienes.

The term "NGF" or "active fragment of NGF" within the sense of the present invention refers to natural NGF, in particular mammalian NGF preferably natural human or murine NGF and all fragments or derivatives of NGF which have its desired biological activity, i.e., prevent the fiber demyelination of oligodendrocytes. Examples of NGF molecules which are suitable for the process according to the present invention are for instance NGF-β, NGF 2.5S or NGF 7S from the submaxillary gland of the mouse. These NGF molecules can, for example, be obtained commercially from Sigma (St. Louis, USA) or Boehringer Mannheim GmbH (Mannheim, Del.). The process according to the present invention is preferably carried out with a human NGF, particularly preferably with human recombinant NGF-β. The production of an active NGF fragment by tryptic digestion of NGF is described by Mercanti et al. in Biochim. Biophys. Acta 496 (1977) 412-419. This fragment is composed of two linear oligopeptides which are linked by a disulfide bridge and contains the amino acid residues 10 to 25 (SEQ ID NO:1) and 75 to 88 (SEQ ID NO:2) of the amino acid sequence of NGF [according to the nomenclature of Angeletti and Bradshaw, Proc. Natl. Acad. Sci. USA 68 (1970) 2417–2421].

The present invention also concerns a pharmaceutical composition for the treatment of diseases in which a demyelination of nerve fibers occurs and which contains NGF or an active fragment thereof as the active substance together with the usual pharmaceutical vehicles, auxiliary substances, fillers and diluents. The pharmaceutical composition preferably contains human NGF, especially human recombinant NGF-β. In addition, the composition can contain one or several pharmaceutically tolerated protease inhibitors, for example, aprotinin, preferably in a kit wherein NGF and said inhibitor are located in separate containers.

In order to produce pharmaceutical preparations, the composition according to the present invention can be processed with therapeutically acceptable vehicles. Suitable vehicles for the production of such solutions are water, polyols, sucrose, invert sugar and glucose. Suitable vehicles for injection solutions are water, alcohols, polyols, glycerol and vegetable oil.

In addition, the pharmaceutical preparations can contain preservatives, solvents, stabilizing agents, wetting agents, emulsifiers, salts for changing the osmotic pressure, buffers and, if desired, other therapeutic drugs.

Inflammatory toxic-metabolic or hypertoxic disorders may cause damage to the myelin sheaths. Examples of such disorders, or diseases, are:

Multiple Sclerosis:
   classical (Charcot type)
   acute multiple sclerosis (Marburg type)
   diffuse sclerosis (Schilder)
   neuroptic myelitis (Devic)
   concentrical sclerosis (Baló)
ADEM (Acute Disseminated Encephalomyelitis and Perivenous Encephalomyelitis:
   (post- and parainfectious, post-vaccinal or "spontaneous")
Demyelination Caused by Virus:
   subacute sclerosing panencepohalitis (SSPE)
   progressive multifocal leucoencephalopathy (PML)
   AIDS-encephalopathy and -myelopathy
   tropical paralysis (HTLV I)
Demyelination Caused by Toxic Metabolism:
   central pontine myclinolysis
   Marchiafava-Bignami syndrome
   funicular myelosis (vitamin B12 deficiency)
Demyelination Caused by Hypoxia/Ischemia:
   subcortical arteriosclerotic encephalopathy (Binswanger's disease)
   post-hypoxic leucoencephalopathy The Guillain-Barre syndrome (B. Vinken, Handbook of Clinical Neurology 7, Diseases of Nerves, Part I, Chapter 19 (1970) pp. 495 et seq.) is the most frequently observed type of peripheral polyneuritis.

Demyelination usually occurs subacutely, or even acutely, whereas slow development taking place over a number of weeks, or even months, is rarely observed. Hence, it is important that when polyneuritis has been diagnosed, treatment with NGF should be initiated immediately so as to prevent demyelination, as is described in the present invention. At the very onset of polyneuritis, as in Multiple Sclerosis, an inflammation of the optic nerve is usually observed. Thus, the present invention is also directed to the treatment of inflammatory diseases of the optic nerve. The action of NGF on the optic nerve is shown in FIG. 3.

Diseases in which a demyelination of nerve fibers occurs and which can be treated with the aid of the pharmaceutical composition according to the present invention can, for example, be caused by inflammation, autoimmune processes, enzymes or toxins. Examples of such diseases are, for instance, Multiple Sclerosis, slow virus encephalitis, various forms of myelitis or heavy metal poisoning. According to the invention it is preferred to administer NGF immediately after an inflammatory disease (causing further a demyelination) of an optic nerve is recognized.

The composition according to the present invention is preferably administered systemically. The administration can be carried out by methods familiar to a person skilled in the art, for example, intrathecally, intravenously or subcutaneously. For the intrathecally or intravenous administration, NGF can be dissolved, for example, in physiological saline.

The addition of protease inhibitors, e.g., aprotinin, is not absolutely necessary when NGF is administered daily but does afford protection against proteases which could inactivate NGF. The preferred lower limit for the daily administered NGF dose is at a concentration between 0.05 µg and 5 µg/kg body weight. The administration of NGF is preferably carried out over a longer time period, i.e., longer than a day, preferably at least 48 hours.

The following examples, references and the figures are provided to aid the understanding of the present invention, the true scope of which is set forth in the appended claims. It is understood that modifications can be made in the procedures set forth without departing from the spirit of the invention.

BRIEF DESCRIPTION OF THE FIGURES

FIGS. 5A, 5B, and 5C show characterization of NGF receptors in marmoset brain by immunohistochemistry. Staining for TrkA is shown at the left (5-μm paraffin-embedded section), and for $p_{75}^{NGFR}$ at the right (30-μm-thick section stained in flotation). FIG. 5A: Both NGF receptors are present in cholinergic neurons of the basal forebrain. Arrows show satellite oligodendrocytes stained for TrkA (left). FIG. 5B: Arrows indicate some of the TrkA- and $p75^{NGFR}$-positive glial cells (astrocytes or microglia) in normal white matter. FIG. 5C: In CNS inflammatory infiltrates, strong staining for both NGF receptors is also apparent on many mononuclear cells and macrophages (arrows). Original magnifications: ×400.

FIG. 6A: MOG-specific T cell proliferative responses in marmoset PBMCs at days 0, 14, and 28 after immunization. FIG. 6B: Serum anti-MOG antibody titers measured by ELISA at day 28 after immunization. The differences between placebo- and rhNGF-treated animals were not statistically significant.

FIGS. 7A, 7B, 7C, and 7D illustrate the effects of rhNGF on cytokine production within the CNS of nonhuman primates. Representative sections from placebo-treated (left) and rhNGF-treated (right) marmosets. (FIG. 7A and FIG. 7B) Staining for IFN-demonstrates the presence of this cytokine in inflammatory mononuclear cells in the center of a perivascular infiltrate from a placebo-treated animal (some designated by arrows); complete suppression is evident in an infiltrate from an rhNGF-treated animal. (FIG. 7C and FIG. 7D) Staining for IL-10, demonstrating strong upregulation of this cytokine in astrocytes of the corpus callosum (normal white matter) in an rhNGF-treated animal. Original magnifications: ×400.

Figure 1A:
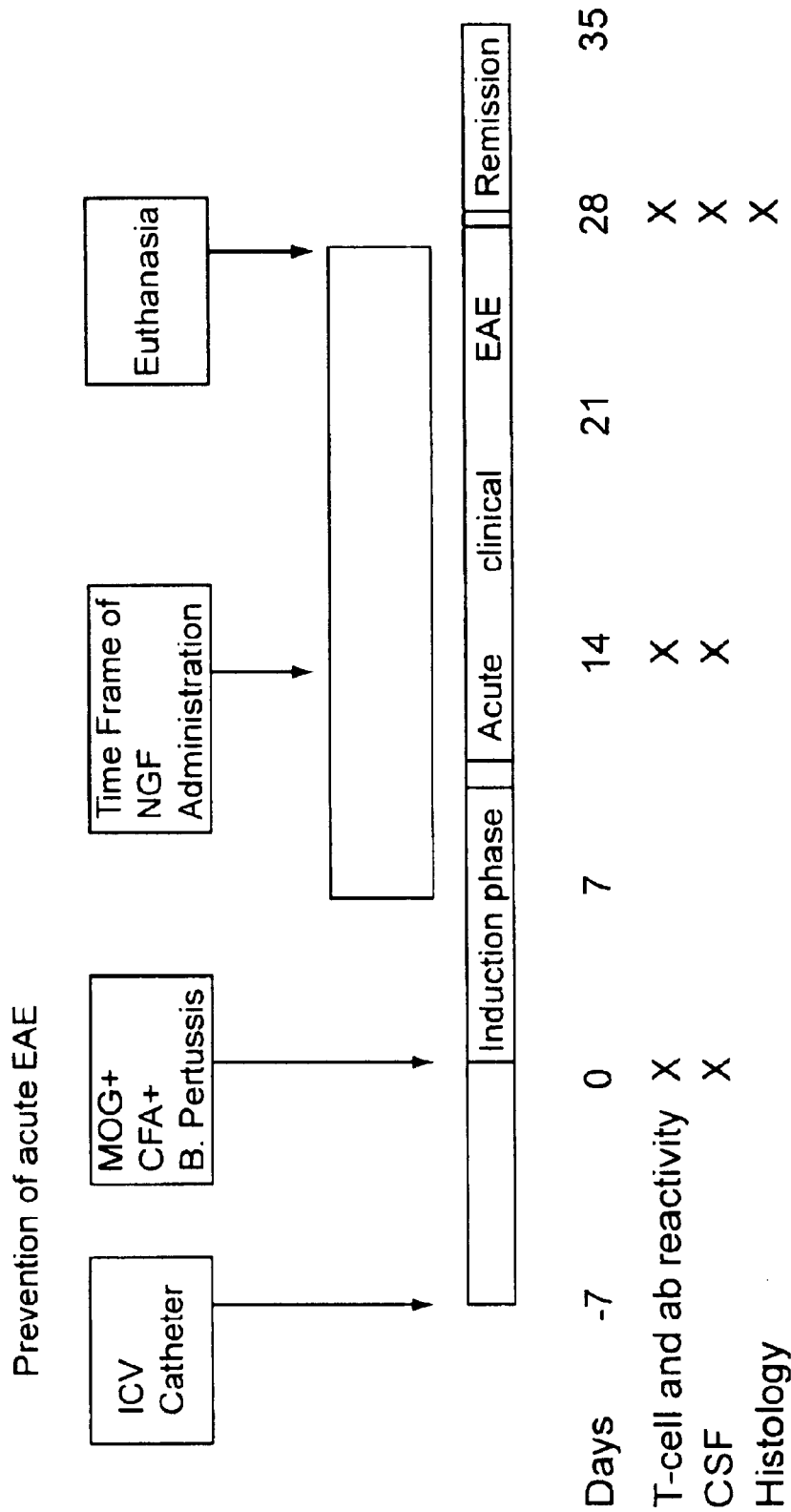
FIG. 1a shows the experimental procedures for preventing acute EAE according to the present invention.
Figure 1B:
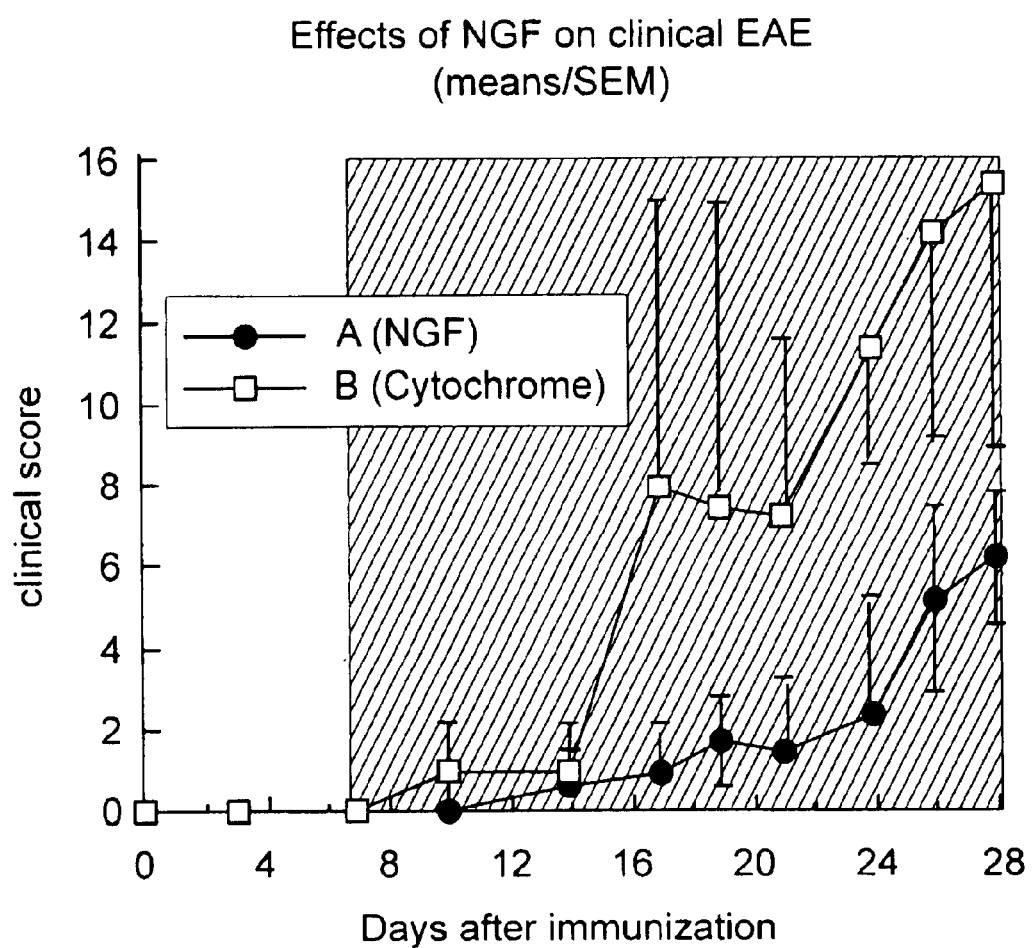
FIG. 1b shows the clinical course of experimental autoimmune encephalomyelitis in placebo (Cytochrom C, n=2) and NGF (n—2) treated animals. The NGF treated animals showed a significant amelioration of the clinical score versus placebo treated animals.
Figure 1C:
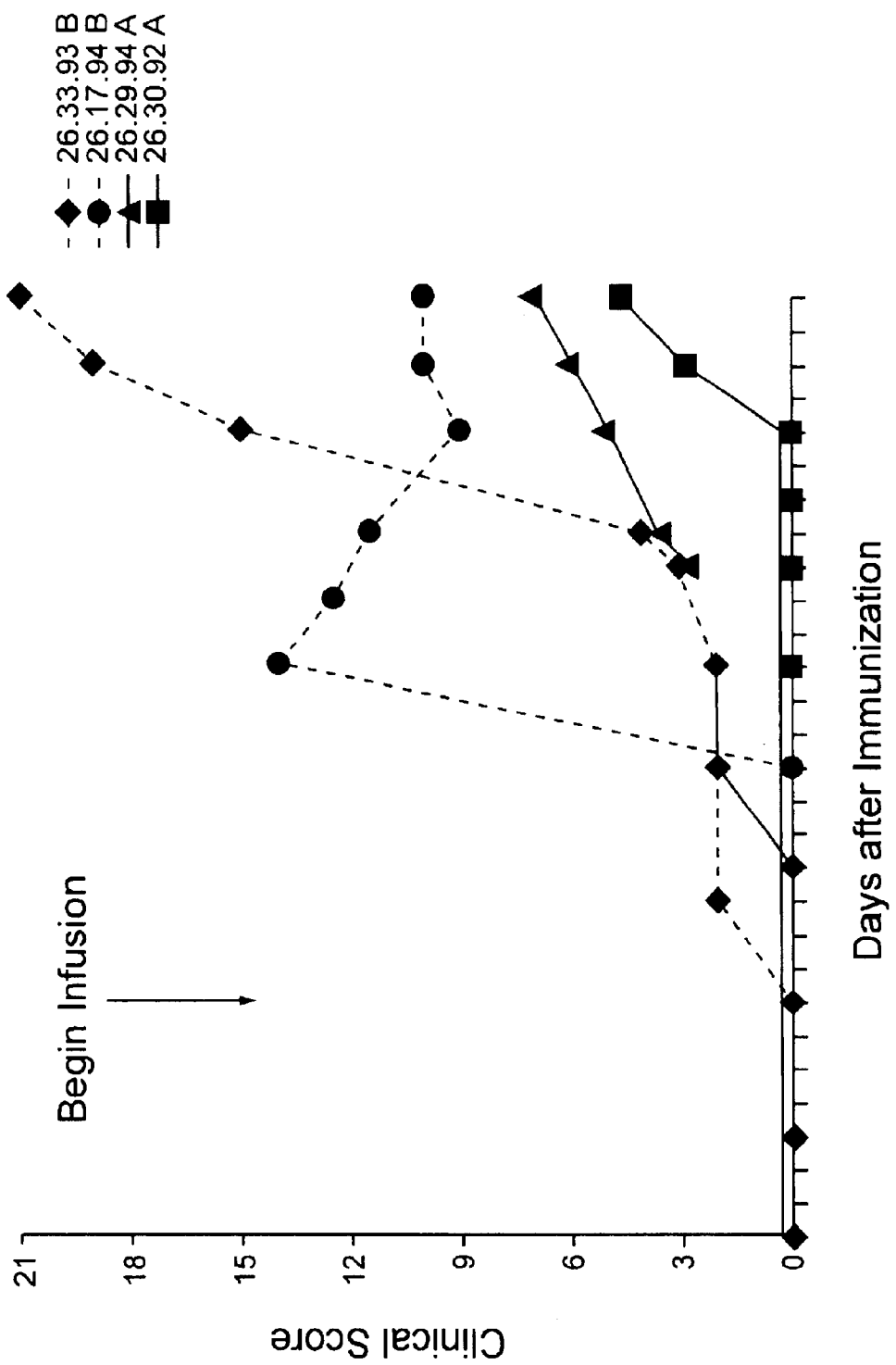
FIG. 1c shows the EAE (experimental allergic encephalomyelitis) reaction in four different marmosets. Marmosets 26.33.93 and 26.17.94 are treated on day 7 after immunization with placebo (cytochrome) whereas marmosets 26.29.94 and 26.30.92 are treated on day 7 after immunization with NGF.
Figure 2:
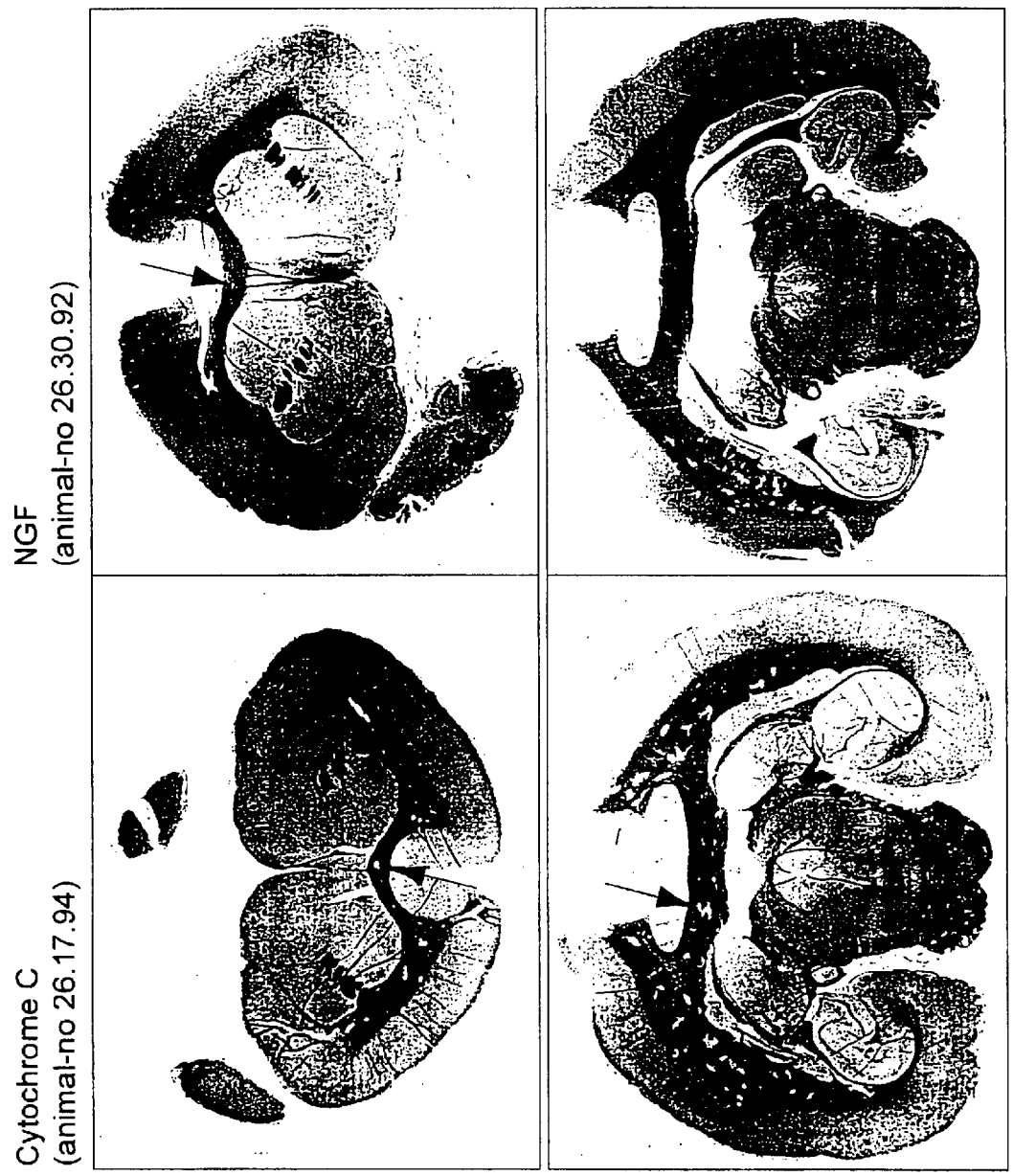
FIG. 2 is a photomicrograph of frontal sections through the brains of marmosets (Luxol Fast Blue Staining), depicting two representative areas from the prosencephalon and mesencephalon. The number of lesions (arrows point to examples in the photomicrographs) is lower in the NGF treated animal than in the marmoset receiving placebo-infusion of cytochrome C (magnification: 4×).
Figure 3:
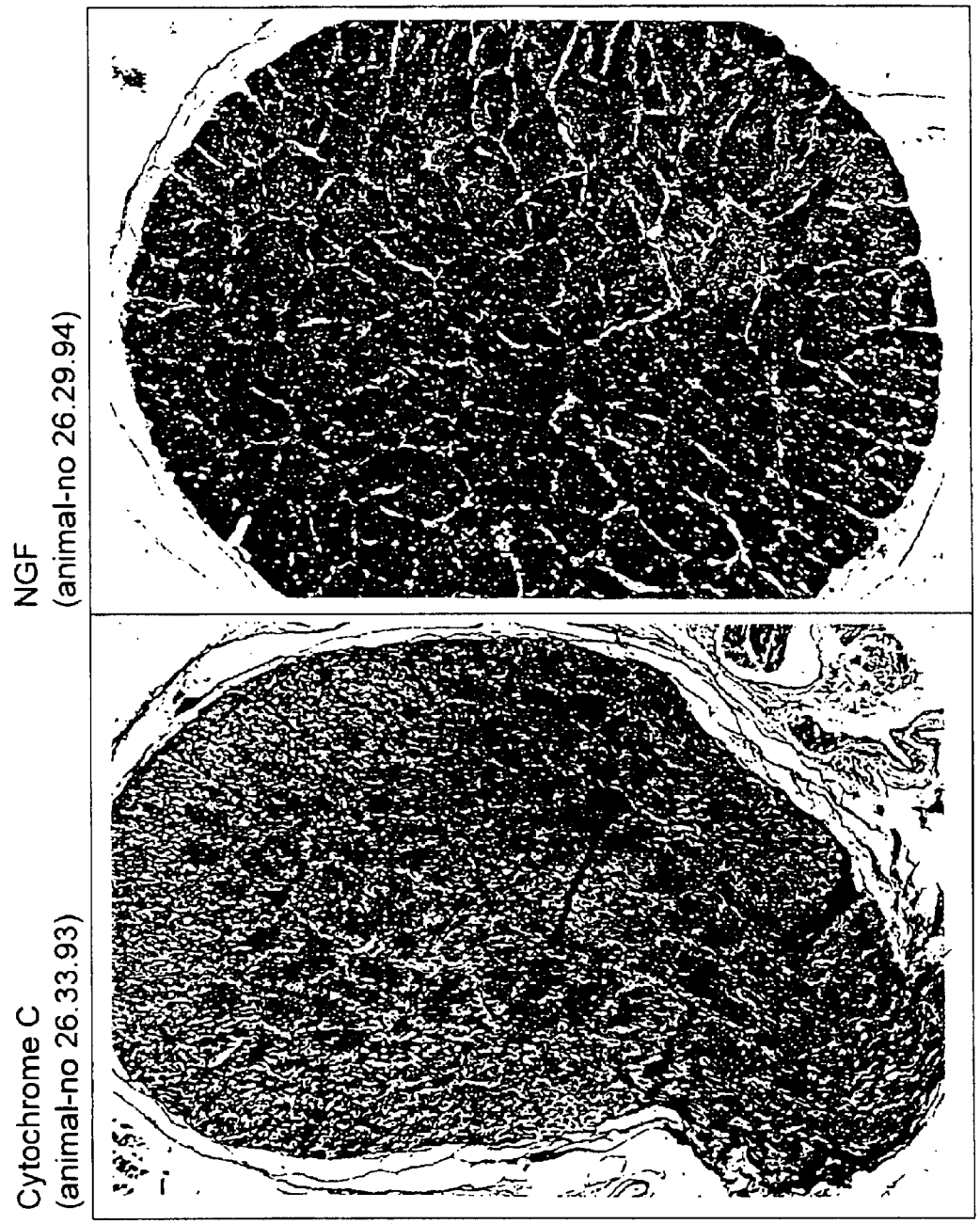
FIG. 3 is a higher magnification of cross sections through the optic nerves of marmosets (Luxol Fast Blue staining). Note the severe inflammation and demyelination in a cytochrome C-treated EAE animal, in contrast to the absence of lesions in the marmoset receiving intraventricular NGF infusion. Magnification: ca. 100×

Preparation of Animals
1. Placement of Intracerebroventricular Catheters

A technique for implanting indwelling cannulas in the brain ventricles of marmosets has been developed. Seven days prior to immunization for EAE, surgery is carried out after the animal is anaesthetized with ketamine/midazolam (20 mg/kg). The skin above the skull is shaved and surgically disinfected with surgical scrub and ethyl alcohol. The animal is positioned in a stereotaxic table on a K-pad and a sterile field is created over the skull. A skin incision is made and the skull exposed. The dura meninges are exposed through a small hole drilled in the bone of the skull, in regard to the appropriate coordinates for the right lateral ventricle (according to a published atlas of marmoset brain anatomy). A 25 gauge 5 mm-long stainless steel guide containing a 35 gauge polycarbonate cannula is then inserted in the cerebral ventricle, and secured to the bone with 2 lateral screws and a thin layer of dental cement. A second skin incision is made in the right flank of the animal. A 25 gauge polyvinyl catheter is connected with the ventricular cannula and then tunneled under the skin to the flank incision. At this point the skull incision is closed with sutures and the flank end of the polyvinyl catheter is connected to the flow regulator of a mini osmotic Alza pump filled with saline. The flank incision is then closed and the animal monitored for recovery. Although no significant risk of infection has been reported using this technique in rodents and higher mammals, Clamoxyl at 10 mg/kg BID per os is administered as a systematic prophylactic procedure against secondary infection of the central nervous system.

2. Replacement of Osmotic Minipumps

For pump replacement, the animal is first sedated (ketamine/midazolam), the hair on one flak trimmed and the skin disinfected using surgical, sterile technique. The animal is placed on a K-pad to prevent hypothermia. A small skin incision (0.5 cm) is made on the flank and the pump connected with the intracerebroventrical catheter and inserted in the subcutaneous space, then the incision is closed with surgical staples. Although no infectious complication has been observed using this technique, Clamoxyl at 10 mg/kg intramuscularly×1 is administered prophylactically at the time of pump insertion. The size of the pump suitable for marmosets is the 200 μl-capacity model 2002, i.e. the smallest available.

EXAMPLE 1
Prevention of acute *C. jacchus* EAE with NGF
1. Immunizations

EAE is induced with 100 μg of rat recombinant myelin/oligodendrocyte glycoprotein (MOG) in complete Freund's adjuvant followed by intravenous administration of $10^{10}$ killed Bordetella Pertussis organisms on the day of immunization and again 48 hours later. In preparation for immunization, antigen and adjuvant are emulsified under sterile conditions. The animal is then anesthetized with keamine/midazolam and 100 μl of the mixture is injected intradermally into four sites in the shoulder and hip areas. Prior to injection the sites are shaved, cleaned three times with surgical scrub and then twice with ethyl alcohol. Bordetella Pertussis is injected slowly (over 5 minutes) after placement of a 21 gauge catheter in the popliteal vein using the same skin preparation technique. A second Bordetella Pertussis injection is given 48 hours later using the same technique.

2. Treatments

Beginning on day 7 after immunization (before the appearance of clinical signs) the animals receive either placebo (cytochrome) or NGF delivered via a cannula implanted in the lateral ventricle and connected by a mini catheter to an osmotic Alza mini pump implanted under the skin of the flank; the pump containing NGF or placebo is implanted on day 0 (to account for the dead volume of the mini catheter) and delivers 6±1 μl/day until day 28. The dose of NGF is 6 μg/day, determined on the basis of preliminary experiments in marmosets. Treatment is continued for a total of 21 days and the animals are euthanized (FIG. 1*a* and table 2).

3. Observation of Clinical Course

Signs of EAE are monitored daily by blinded observers. Proliferative responses to myelin antigens are measured in blood on days 0, 14 and 28 after immunization. The CSF inflammatory responses and the CSF concentrations of NGF are monitored at days 0, 14 and 28 after immunization.

4. Histologic Examination

Neuropathologic examination of the brain and spinal cord is performed according to standard published techniques. Animals are euthanized at the end of the 28 day period and the nervous system perfused. Under deep pentobarbital anesthesia a thoracotomy is performed and a 14 gauge catheter is introduced and secured in the left ventricle. The right atrium is then opened and 200 ml of cold phosphate buffered saline are perfused through the heart. The descending aorta is then clamped in order to preserve spleen, inguinal lymph nodes, and the lower portion of the spinal cord as a supply of fresh or cryopreserved tissues for immunologic studies. Two hundred ml of a 2.5% solution of glutaraldehyde in phosphate buffer, pH 7.4 are then perfused as fixative. Brain hemispheres and spinal cord are dissected and after further fixation are prepared for histopathologic analysis according to our standard protocol. Eight 2.5 mm thick sections are cut in a plane perpendicular to the intercallosal line and embedded in paraffin for cutting and routine stains (hematoxylin/eosin and luxol fast blue). Some tissue is saved for processing thin (plastic) sections and electron microscopy, in order to obtain an ultrastructural analysis of myelin. Immunohistochemistry is performed on fixed tissues or on cryopreserved specimens from the caudal spinal cord, including staining with anti-MOG, anti-PLP and anti-MAG antibodies. In addition to ultrastuctural analysis, these studies provide a valid assessment of the remyelinating process, if any, in and around the inflammatory lesions.

5. Cytokine Gene Expression in the Central Nervous System

These studies are carried out on fresh frozen sections of the spinal cord. Semi-quantitation of tumor necrosis factor (TNF-$\alpha$), lymphotoxin (TNF-$\beta$), IL-2, IL-6, IL-10 and transforming growth factor-(TGF-$\beta$) are performed according to the protocol in use at the UCSF laboratory. Previous work has already established that the proinflammatory cytokine TNF-$\alpha$ likely plays a major role in promoting inflammation and demyelination in marmoset EAE. This proposed approach acts as a preliminary screen to determine whether the NGF-induced protection against EAE is mediated via modulation of local cytokines-in the nervous system.

6. Treatment Groups

There are two experimental groups used:
a) NGF, 6 µg/day intracerebroventricularly
b) Placebo (Cytochrome c), 6 g/day intracerebroventricularly Treatments begin 7 days after immunization and are continued until day 28 after immunization.

LIST OF REFERENCES

Althaus et al., Neurosci. Lett. 135 (1992) 219–223
Angeletti and Bradshaw, Proc. Natl. Acad. Sci. USA 68 (1970) 2417–2421
Chun, L. L. Y., and Patterson, P. H., J. Cell Biol. 75 (1977) 694–704
Chun, L. L. Y., and Patterson, P. H., J. Cell Biol. 75 (1977) 705–711
Crain, S. M., and Peterson, E. R., Brain Res. 79 (1974) 145–152
Gage et al., J. Comp. Neurol. 269 (1988) 147–155
Hefti et al., J. Brain Res. 293 (1986) 305–311
Hefti et al., J. Neurosci. 6 (1986) 2155–2162
International Application No. WO 93/03140
Kandel et al., Principles of Neural Science, 3rd Ed., Elsevier 1991, p. 22
Levi-Montalcini, R., and Angeletti, P. U., Dev. Biol. 7 (1963) 653–659
Massacesi, L. et al., Ann. Neurol. 37 (1995) 518–530
Vinken, B., Handbook of Clinical Neurology 7, Diseases of Nerves, Part I, Chapter 19 (1970) pp. 495 et seq.

EXAMPLE 2

Human Nerve Growth Factor Protects Common Marmosets against Autoimmune Encephalomyelitis by Switchng the Balance of T Helper Cell Type 1 and 2 Cytokines within the Central Nervous System Multiple sclerosis is a demyelinating disorder of the central nervous system (CNS), in which an immune attack directed against myelin constituents causes myelin destruction and death of oligodendrocytes, the myelin-producing cells. In this example, the efficacy of nerve growth factor (NGF), a growth factor for neurons and oligodendrocytes, in promoting myelin repair was evaluated using the demyelinating model of experimental allergic encephalomyelitis (EAE) in the common marmoset. We found that NGF delayed the onset of clinical EAE and pathologically, preventing the full development of EAE lesions. We demonstrate by immunocytochemistry that NGF exerts its antiinflammatory effect by downregulating the production of interferon by T cells infiltrating the CNS, and upregulating the production of interleukin 10 by glial cells in both inflammatory lesions of EAE and normal-appearing CNS white matter. Thus, NGF, currently under investigation in human clinical trials as a neuronal trophic factor, may be an attractive candidate for therapy of autoimmune demyelinating disorders.

Introduction.

Multiple sclerosis (MS) is a chronic, relapsing-remitting disease of the central nervous system (CNS) white matter characterized pathologically by perivenular infiltration of mononuclear cells and macrophages, demyelination with astrocyte proliferation and gliosis, and death of the oligodendrocytes (1). Based in part on analogy with the disease model experimental allergic encephalomyelitis (EAE), MS is thought to be an autoimmune disorder mediated by autoaggressive T cells that recognize myelin antigens in the context of class II HLA molecules (2). However, because neither the putative antigens that trigger these autoimmune responses nor the precise mechanisms responsible for demyelination in human MS have been unequivocally identified, the design of therapies that aim to prevent myelin destruction remains a challenge (2).

Nerve growth factor (NGF), a pleiotropic cytokine of the neurotrophin family, promotes the biosynthesis of myelin by oligodendrocytes in the CNS (3) (4) and by Schwann cells in the peripheral nervous system (5). These myelin-promoting effects of NGF appear to be mediated by the high affinity NGF receptor TrkA rather than by the low affinity NGF receptor p75NGFR (6) (7). In addition to its role in myelination, neuronal growth, and CNS differentiation (8), NGF is known to have pleiotropic effects on various cells of the immune system (9). The immunomodulatory properties of NGF, and its trophic effects on myelin-producing cells, provide a framework for the use of NGF in the treatment of immune-mediated demyelinating disorders. Here, we report that therapy with recombinant human (rh)NGF protects against CNS inflammation and demyelination in a nonhuman primate model of EAE, the common marmoset *Callithrix jacchus*. This antiinflammatory effect of NGF has not been previously reported, and appears to be mediated by an alteration of the balance between Th1 and Th2 cytokines within the CNS.

Materials and Methods

Animals and Treatment Groups.

C. jacchus marmosets were maintained in a primate colony at the University of California, San Francisco, and were cared for in accordance with all institutional guidelines. Phlebotomy and cerebrospinal fluid (CSF) collection were performed under anesthesia in accordance with standard approved protocols. For intracerebroventricular administration of treatments, a sterile 36-gauge polycarbonate cannula secured inside a stainless steel brain cannulation device (Alzet) was stereotaxically implanted into the right lateral cerebral ventricle under anesthesia with isoflurane (coordinates: AP 6 mm, L 1.25 mm, V 7 mm, relative to bregma (10)). The cannula was secured to the skull with miniature bone screws and dental acrylic cement, and connected by a 28-gauge polyvinyl tubing tunneled under the skin to an osmotic minipump (model 2004; Alzet) delivering 0.9% NaCl and implanted subcutaneously on the right flank. 7–14 d after surgery, on the day when EAE was induced, subcutaneous treatment minipumps containing either rhNGF or cytochrome c (CYT) as a placebo (Boehringer) at a concentration of 1 mg/ml were substituted. The minipumps delivered 6 µl/d, and due to the dead volume of the tubing connecting the minipump and the brain cannula, drugs were delivered beginning 7 d after immunizations and until completion of the experiments.

Induction and Assessment of EAE.

EAE was induced by active immunization with 100 µg of a recombinant protein corresponding to the extracellular domain of rat MOG (rMOG) in combination with CFA and Bordetella pertussis as described previously (11). Clinical signs of EAE were recorded daily by an observer blinded to the treatment groups using a grading scale specifically developed for marmosets in our laboratory (Table 1). 28 d after immunization, animals were killed under deep phenobarbital anesthesia by intracardiac perfusion with PBS followed by either 4% buffered paraformaldehyde or 3% paraformaldehyde/0.2% glutaraldehyde. Brain hemispheres, optic nerves, and spinal cord were removed and dissected in 1-mm-thick consecutive blocks, which were paraffin-embedded for routine histology and/or cryopreserved and stored at −80° C. for immunocytochemistry. Pathological scores were assigned to paired sections throughout the entire neuraxis, using a grading scale to quantitate inflammation and demyelination: 0, normal; +, rare (1–3/section) perivascular cuffs with minimal demyelination; ++, 3–10 perivascular cuffs/section accompanied by moderate demyelination; +++, widespread perivascular cuffing, extensive demyelination with large confluent lesions.

Immunocytochemistry.

Sections of brain and spinal cord (5–30 µm) were pretreated with 1% H2O2 in Tris-Cl buffer, and blocked with 5% normal goat serum (Vector Laboratories) and 0.3% Triton X-100 for 60 min. Sections were incubated in sequence with the primary antibodies overnight at 4° C., an appropriate biotinylated secondary antibody, and avidin-horseradish peroxidase complex (Vectastain ABC; Vector Laboratories), then developed with 3, 3o-diamino-benzidine (Sigma-Aldrich) and counterstained with hematoxylin (Research Genetics). The primary antibodies and their working dilutions were as follows: for NGF receptors, rabbit anti-rat TrkA (RTA), 1:1,000; rabbit anti-mouse p75NGFR (Rex), 1: 1,000 (both provided by Dr. Louis Reichardt, University of California, San Francisco); rabbit anti-human TrkA (Sc 118; Santa Cruz Biotechnology, Inc.), 1:1,000; mouse anti-human p75NGFR (Boehringer), 1:1,000; for cytokines, mouse anti-monkey IFN-(MD1; U-Cytech), 1:50; and mouse anti-human IL-10 (MCA B-S10; Instruchemie), 1:100. Slides stained for IFN- and IL-10 were pretreated by overheating in a microwave for retrieval of antigens. For each cytokine, four consecutive slides on two sections from each animal were stained, which included an average of 12±10 (mean±SD) inflammatory infiltrates per slide; quantitation of infiltrates and positively stained cells was done using a grid of 250×250 µm.

TABLE 1

Expanded Disability Status Scale for Marmoset EAE

| Function | Disability Score | Maximal Score |
| --- | --- | --- |
| 1 Alertness | 0: normal; 1: reduced; 2: lethargic | 2 |
| 2 Spontaneous mobility | 0: normal; 1: mild slowing; 2: marked slowing; 3: absent | 3 |
| 3 Tremor | 0: none; 1: moderate; 2: severe | 2 |
| 4 Tone* | 0: normal; 1: mildly reduced; 2: markedly reduced; 3: absent | 12 |
| 5 Motor (grip)* | 0: normal; 1: mildly reduced; 2: markedly reduced; 3: absent | 12 |
| 6 Sensory* Light touch Pain‡ | Light touch 0: normal; 1: reduced; 2: absent 8 Pain 0: normal; 1: reduced; 2: absent | 8‡ |
| 7 Eye movements | 0: normal; 1: abnormal | 1 |
| 8 Vision (including pupillary reflex) | 0: normal; 1: abnormal; 2: absent | 2 |
| 9 Vocalization | 0: normal; 1: changed 1 | |
| 10 Bladder function | 0: normal; 1: abnormal | 1 |
| 11 Other signs | 0: normal; 1: abnormal | 1 |

*Scored in each limb
‡Scored only if tactile not present.
The total score is derived by adding the scores for each system. The maximal score for the scale is 45.

Bioassay for rhNGF.

CSF levels of rhNGF were determined using a specific bioassay of cell survival in primary cultures of neural crest-derived chicken embryonic sensory neurons (12). In brief, dorsal root ganglia neurons were extracted from embryos, cultured in F14 medium with 10% horse serum and antibiotics, and then seeded onto poly-omithine/laminin-coated wells in microtiter plates in the presence or absence of known concentrations of rhNGF, or aliquots of CSF (10–50 µl). Neuronal survival was assessed after 48 h by counting the number of surviving neurons with neurite elongation under a phase-contrast microscope. Neurotrophic activity was expressed as one half of the maximal stimulation index (EC50), e.g., 100 pg/ml for rhNGF.

Assessment of Peripheral Immune Reactivity.

T cell proliferative responses were performed using a standard 3H[thyrnidine] incorporation assay with 2×105 freshly isolated marmoset or human PBMCs (11) incubated with the following: no antigen; rMOG, 10 µg/ml; PHA, 2 µg/ml; killed *Staphylococcus aureus* Cowan strain (SAC), 1:10,000; LPS, 20 ng/ml; or rhNGF, 100 ng/ml. Stimulation indices were calculated as the ratio of 3H[thymidine] incorporation in stimulated to unstimulated (medium alone) wells. Serum antibody responses were tested by ELISA in 96-well plates coated with 1 µg rMOG/well using 100 µl of serum dilutions of *C. jacchus* sera and 100 µl of peroxidase-conjugated anti-monkey IgG (1:4,000; Sigma-Aldrich) (11). Plates were developed with o-phenylenediamine-peroxidase substrate and read at 490 nm in a Vmax ELISA reader (Molecular Devices).

Flow Cytometry.

Staining for flow cytometry studies was performed after blockade of Fc receptors with PBS plus 1% BSA and 10% goat serum (Vector Laboratories). Cells were stained with the following antibodies and the appropriate isotype controls: 20 µl unconjugated goat anti-human TrkA or mouse anti-human p75NGFR antibody followed by FITC-conjugated anti-goat or anti-mouse IgG (Jackson ImmunoResearch Laboratories); double staining was performed with PE-conjugated anti-CD4 (Beckman-Coulter), CD20 (Immunotech), or CD14 (Beckman-Coulter). Samples were analyzed in a Becton Dickinson FACScan™ apparatus, and data analysis was done by subtracting isotype control percentage from experimental percentage.

Statistical Analysis.

Clinical and histological scores in the treatment groups were compared with the Mann-Whitney sum rank test, using StatView II software (Abacus). Quantitative immunohistochemistry for IFN- and IL-10 was analyzed by the Student's t test. A P value 0.05 was considered significant. Results are expressed as mean±SD.

Results and Discussion

NGF Inhibits the Development of EAE in *C. jacchus* Marmosets.

Beginning 7 d after induction of EAE, *C. jacchus* marmosets were randomly assigned to treatment with either rhNGF or CYT as placebo administered via the intracerebroventricular cannula. In this experimental design, we chose to use an intracranial route to ensure accurate delivery of the drug into the CNS. This resulted in sustained elevated concentrations of rhNGF in the CSF of all rhNGF-treated animals (2–300 ng/ml), as measured by a specific bioassay.

Consistent with previous experience in MOG-sensitized marmosets (11), six placebo (CYT)-treated animals developed moderate to severe clinical signs of EAE beginning 10–16 d after immunization. Clinical signs in most of these animals progressed by the end of the study (day 28 after immunization). By contrast, a total of six rhNGF-treated marmosets showed either no clinical signs or a markedly attenuated disease course (Table 2). In those rhNGF-treated animals that developed clinical signs, the onset of EAE was delayed compared with controls (day 21±0.9 vs. day 11±0.4 after immunization, P=0.02). Maximal clinical scores observed averaged 12.5±2.3 in controls vs. 2.6±0.9 in rhNGF-treated animals (P=0.01).

TABLE 2

Clinical Findings in rhNGF- and Placebo-treated Animals

|  | Onset of EAE | | Maximal clinical | |
| --- | --- | --- | --- | --- |
|  | Day pi | Score | score | (Day pi) |
| rhNGF group | | | | |
| 26.30.92 | 28 | 2 | 2 | (28) |
| 26.29.94 | 14 | 3 | 6.5 | (28) |
| UC5.95 | 20 | 3.5 | 4 | (27) |
| 101 | 19 | 2 | 2.5 | (18) |
| 231.90 | — | 0 | 0 | (—) |
| FL 5.96 | 21 | 1 | 1 | (21) |
| Placebo group | | | | |
| 26.17.94 | 17 | 11 | 14 | (17) |
| 26.33.93 | 10 | 2 | 21 | (28) |
| 157.94 | 7 | 2 | 5 | (19) |
| 198.94 | 7 | 2 | 14.5 | (28) |
| FL 3.95 | 15 | 1 | 7.5 | (28) |
| FL 6.96 | 14 | 1 | 13 | (19) | pi, post immunization.

Figure 4B:
FIGS. 4A and 4B illustrate representative neuropathological findings in placebo-(FIG. 4A) and rhNGF-treated (FIG. 4B) animals at the completion of the study (day 28 after immunization). Gross anatomical views of coronal sections through the temporal lobe illustrate multiple demyelinating plaques disseminated throughout the subcortical white matter in the control. In the rhNGF-treated animal, the density of plaques is markedly reduced. The paraffin-embedded sections were stained with Luxol Fast blue periodic acid-Schiff.
Figure 4A:

Neuropathological evaluation confirmed the observed clinical protection. Placebo-treated animals displayed typical large perivascular infiltrates comprised of mononuclear cells and macrophages accompanied by extensive concentric demyelination with gliosis widely distributed throughout the CNS. In rhNGF-treated marmosets, the number and size of the inflammatory infiltrates were reduced and demyelination was minimal (FIG. 4, and Table 3). Although differences in severity and in the affected CNS regions existed between individual marmosets, the disease burden was greatly reduced in animals treated with rhNGF compared with controls. In both treatment groups, the amounts of demyelination and inflammation were concordant. Thus, treatment with rhNGF inhibited the development of inflammatory demyelination in marmosets.

TABLE 3

Neuropathological Findings

| Animal | CNS Region | | | | | | |
|---|---|---|---|---|---|---|---|
| | Subcortical white matter | Corpus callosum | Optic chiasm, nerves, and tracts | Brain stem, cerebellum | Cervical spinal cord | Thoracic spinal cord | Lumbar spinal cord |
| rhNGF group | | | | | | | |
| 26.30.92 | ++ | + | ++ | 0-+ | + | + | 0 |
| 26.29.94 | + | 0-+ | 0-+ | 0 | 0 | 0-+ | 0-+ |
| UC5.95 | 0 | + | 0 | 0 | + | 0 | 0 |
| 101 | 0 | 0 | 0 | 0 | + | 0 | 0 |
| 231.90 | + | 0 | + | + | + | + | + |
| FL 5.96 | + | ++ | + | 0 | 0 | 0 | 0 |
| Placebo Group | | | | | | | |
| 26.17.94 | +++ | ++ | +++ | ++ | +++ | +++ | ++ |
| 26.33.93 | +-++ | +-++ | +++ | +-++ | +++ | +++ | ++-+++ |
| 157.94 | 0 | 0 | +++ | 0 | ++ | 0 | 0 |
| 198.94 | + | 0 | + | 0 | +++ | ++-+++ | ++ |
| FL 3.95 | 0 | + | ++ | + | ++ | 0 | 0 |
| FL 6.96 | 0 | + | 0 | 0 | ++ | 0 | 0 |

Paired CNS sections were scored using a combined scale for inflammation and demyelination (0 to +++; see Materials and Methods).

Several considerations dictated the choice of the *C. jacchus* model of EAE for this study. First, this nonhuman primate species is best suited to test the efficacy of the human NGF protein, due to potential species-related differences in the expression of the NGF receptors TrkA and p75NGFR (13). Second, pathological features of rMOG-induced EAE in *C. jacchus* include moderate CNS inflammation, an early demyelinating component, and significant remyelination, all characteristics found in human MS. Third, the mechanisms of demyelination in *C. jacchus* EAE and MS are similar and involve vesicular disruption of myelin mediated by autoantibodies that recognize MOG (14). Treatment with rhNGF was begun 7 d after immunization, presumably at a stage of EAE where immune responses against the immunizing antigen had already developed. We had hypothesized that in this experimental design the effect of treatment, if any, would be to promote clinical recovery and remyelination in the rhNGF-treated animals. Surprisingly, rhNGF prevented the initial development and delayed the onset of clinical signs of EAE, and suppressed both the inflammatory and demyelinating components of CNS pathology. Because most of the rhNGF-treated animals displayed only minimal demyelination, it was not possible to assess differences in remyelination.

Based on in vitro observations in rodents, several growth factors with trophic and survival effects on oligodendrocytes have been considered for therapy in demyelinating disorders, including insulin-like growth factor (IGF)-1, glial growth factor (GGF)-2, platelet-derived growth factor, ciliary neurotrophic factor, and fibroblast growth factor (15). In vivo, both IGF-1 and GGF-2 (15) (16) have been shown to be capable of reducing disease severity in murine EAE; however, exacerbation of disease has also been described with IGF-1 (17). It is important to recognize that, due to the interspecies differences in the biological effects of growth factors and the differential expression of their specific receptors, information derived from rodent studies may not be applicable to humans. Our study clearly demonstrates that NGF protects against CNS inflammatory and demyelinating disease in a nonhuman primate species that is known to develop EAE lesions that are indistinguishable from acute lesions of MS (14). Although NGF has been shown to ameliorate experimental allergic neuritis (18), to our knowledge this growth factor has not been tested in rodent EAE and it is possible that its protective effect is restricted to primate species.

Mechanisms Responsible for the Protective Effects of NGF.

Expression of NGF receptors in the CNS of marmosets was studied by immunocytochemistry, using antibodies against human or rat surface antigens. Both the high affinity NGF receptor (TrkA) and the low affinity NGF receptor (p75NGFR) were detected in marmoset basal forebrain neurons, indicating that these antibodies fully cross-reacted with *C. jacchus* NGF receptors (FIG. 5A). In CNS white matter, widespread expression of TrkA and p75NGFR was detected in cells that had the morphologic appearance of astrocytes and/or microglial cells (FIG. 5B) and in oligodendrocytes (not shown). In addition, a proportion of the mononuclear cells and macrophages comprising the inflammatory infiltrates of EAE lesions were positive for TrkA and p75NGFR (FIG. 5C). Expression of NGF receptors on marmoset immune cell subsets was studied by FACS® analysis, using double staining of PBMCs. Both the TrkA receptor and the p75NGFR were widely expressed in CD4+T cells (52 and 67%, respectively), monocytes (57 and 56%), and in a small subpopulation of B cells (6 and 9%) (data not shown). Thus, in this nonhuman primate system, glial and inflammatory cells within the CNS and a large proportion of immune cells in the periphery expressed NGF receptors, raising the possibility that several regulatory pathways may have participated in the protective effect of NGF on EAE.

Figure 6A:
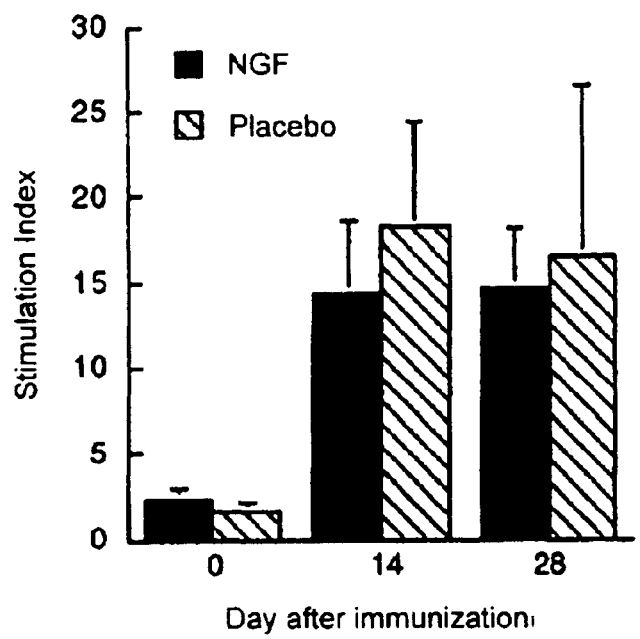
FIGS. 6A and 6B show serial measurements of T cell and antibody reactivity against MOG during the course of EAE in placebo- and rhNGF-treated marmosets.
Figure 6B:
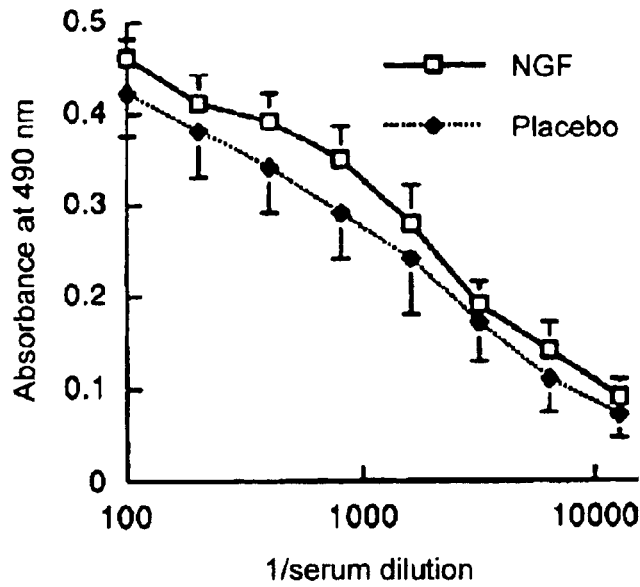

To assess whether treatment with rhNGF modified the response of the peripheral immune system to the immunizing antigen, MOG-induced proliferative responses in PBMCs and serum anti-MOG antibody titers were monitored at days 0, 14, and 28 of the study. MOG-specific proliferative responses and anti-MOG antibody titers were similar in rhNGF- and placebo-treated animals (FIG. 6), indicating that peripheral T cell and B cell responses were not affected by intracerebral administration of NGF. Additional experiments using PBMCs and macrophages isolated from normal subjects and stimulated with PHA, SAC, or LPS in the presence or absence of exogenous rhNGF (1–1,000 ng/ml) confirmed that rhNGF did not interfere with either proliferative responses or macrophage reactivity. Finally, the expression of NGF receptors on subsets of PBMCs was not modified by preincubation with exogenous rhNGF at concentrations ranging from 1 to 1,000 ng/ml (data not shown). Taken together, these data suggest that treatment with NGF inhibited the development of EAE through interference with effector mechanisms of EAE pathology rather than through modulation of the induction phase of EAE.

Cytokines produced by T cells may profoundly influence the course of autoimmune disorders (19). In rodents and in marmosets, CNS inflammation results from the priming of Th1 cells that secrete proinflammatory cytokines such as TNF- and IFN-. Conversely, EAE can be inhibited by immunosuppressive cytokines (IL-4, IL-5, IL-10, and TGF-β) produced by Th2 cells (for a review, see reference 2). In the current study, we examined the expression of IFN- and IL-10 within the CNS of placebo- and NGF-treated marmosets by immunocytochemistry. Results are presented in FIG. 7 and Table 4. In agreement with the scores of standard histological analysis, placebo-treated controls had significantly more infiltrates than rhNGF-treated animals (20.2±9.0 vs. 7.3±8.0, respectively). Consistent with a Th1 response, IFN- was expressed at high levels by infiltrating inflammatory cells in these controls. In marked contrast, IFN- was mostly absent from perivascular inflammatory cuffs in rhNGF-treated marmosets (FIG. 7A and FIG. 7B). An opposite pattern was seen for the expression of IL-10, which was markedly upregulated in inflammatory infiltrates of rhNGF-treated animals compared with controls. Quantitative analysis confirmed that these differences between the two treatment groups were significant, with the exception of the absolute number of IL-10-positive inflammatory cells per infiltrate (Table 4). This was because IL-10 was expressed in lesions from controls, which included more inflammatory cells than infiltrates from rhNGF-treated animals. However, the percentage of IL-10positive cells per infiltrate was increased in rhNGF-treated marmosets (Table 4). In addition to inflammatory lesions, IL-10 was distinctly expressed at high levels in glial cells of normal-appearing white matter in NGF-protected marmosets. These cells had the morphology of astrocytes, although activated microglia cannot be formally excluded, and did not express IFN- (FIG. 7C and FIG. 7D; Table 4). Taken together, these results indicate that the protective effect of NGF was mediated through local modulation of the intracerebral network of cytokines produced by inflammatory cells of the perivascular infiltrates, and by glial cells in the unaffected CNS white matter.

The production of NGF is increased in a variety of CNS disorders, including brain injury (20), acute rodent EAE (21), and during the relapsing phase of MS (22). These conditions are associated with the presence of cytokines that stimulate the production of NGF by astrocytes, such as IL-1, TNF- (23), IL-4, and IL-5 (24), which perhaps represents a physiological response to tissue injury (25). Our observation that NGF in turn can modulate cytokine expression by inflammatory and glial cells in EAE underlines the importance of this molecule as a potent autocrine, antiinflammatory cytokine produced within the blood-brain barrier. The effect of NGF on IL-10 expression appears similar to that reported for the neuroregulin GGF-2 (16), and may be a common immunomodulatory pathway for several CNS growth factors. In diseases like EAE and MS, presentation of myelin antigens to T cells is dependent on the expression of class II HLA molecules on astrocytes and macrophages/microglia, which is upregulated by IFN- (26) and down-regulated by IL-10 (27). Thus, a possible effector mechanism for the protective action of NGF could be decreased HLA class II expression within the CNS, either indirectly through its effects on IFN- and IL-10 production or by a direct effect on astrocytes (28). Indeed, further investigations are needed in this primate system with close phylogenetic similarity to humans, to determine whether the effects of NGF on CNS cytokine production provide long-term benefit in a chronic experimental design. In light of recent evidence suggesting a role for neuronal damage as a mechanism participating in the pathogenesis of MS lesions (29) (30), NGF or agonist compounds could represent a novel therapeutic alternative for demyelinating disorders that combines the benefits of neuroprotection and modulation of CNS autoimmunity.

TABLE 4

Quantitative Immunohistochemistry of Cytokines in the CNS of rhNGF- and Placebo-treated Animals

| | Perivascular Infiltrates | | | | Normal white matter |
|---|---|---|---|---|---|
| Cytokine examined | No. of infiltrates analyzed/cm² | No. of stained mononuclear cells/grid | (Percentage of total)* | No. of stained glial cells/grid | No. of stained glial cells/grid |
| IFN-γ | | | | | |
| placebo | 5.1 ± 2.4 | 14.0 ± 13.0 | (14.6 ± 14.0) | 0 | 0 |
| rhNGF | 1.3 ± 1.5 | 1.8 ± 2.0 | (0.3 ± 0.7) | 0 | 0 |
| P value‡ | 0.004 | 0.020 | 0.020 | — | — |
| IL-10 | | | | | |
| placebo | 5.3 ± 2.6 | 7.3 ± 0.1 | (4.8 ± 4.0) | 1.5 ± 1.3 | 1.1 ± 1.6 |
| rhNGF | 3.1 ± 2.8 | 10.0 ± 1.74 | (23.3 ± 16.0) | 24.1 ± 12.0 | 10.1 ± 2.1 |
| P value‡ | 0.050 | 0.400 | (0.036) | 0.007 | <0.0005 |

*Percentage of positively stained cells relative to total number of mononuclear cells.
‡rhNGF vs. placebo.

REFERENCES

1. Raine, C. 1997. Demyelinating diseases. In Davis R., Robertson D., eds. Textbook of Neuropathology. 3rd ed Baltimore, Williams & Wilkins, 627–714.
2. Hohlfeld, R. 1997. Biotechnological agents for the immunotherapy of multiple sclerosis. Principles, problems and perspectives. Brain. 120:865–916[Abstract].
3. Althaus, H., Kloppner, S., Schmidt-Schultz, T., Schwartz, P. 1992. Nerve growth factor induces proliferation and enhances fiber regeneration in oligodendrocytes isolated from adult pig brain. Neurosci. Lett. 135:219–223 [Medline].
4. Cohen, R., Marmur, R., Norton, W., Mehler, M., Kessler, J. 1996. Nerve growth factor and neurotrophin-3 differentially regulate the proliferation and survival of developing rat brain oligodendrocytes. J. Neurosci. 16:6433–6442[Abstract/Full Text].
5. Urschel, B., Hulsebosch, C. 1990. Schwann cell-neuronal interactions in the rat involve nerve growth factor. J. Comp. Neurol. 296:114–122[Medline].
6. Bothwell, M. 1995. Functional interactions of neurotrophins and neurotrophin receptors. Annu. Rev. Neurosci. 18:223–253[Medline].
7. Carter, B., Lewin, G. 1997. Neurotrophins live or let die: does p75NTR decide? Neuron. 18: 187–190[Medline].
8. Lewin, G., Barde, Y. 1996. Physiology of the neurotrophins. Annu. Rev. Neurosci. 19:289–317[Abstract].
9. Levi-Montalcini, R., Skaper, S., Dal Toso, R., Petrelli, L., Leon, A. 1996. Nerve growth factor: from neurotropin to neurokine. Trends Neurosci. 19:514–520[Medline].
10. Stephan, H., Baron, G., Schwerdtfeger, W. 1980. The brain of the common marmoset (*Callithrix jacchus*). A stereotaxic atlas. Berlin/Heidelberg/New York, Springer-Verlag, pp. 93 pp.
11. Genain, C. P., Nguyen, M. H., Letvin, N. L., Pearl, R., Davis, R. L., Adelman, M., Lees, M. B., Linington, C., Hauser, S. L. 1995. Antibody facilitation of multiple sclerosis-like lesions in a non human primate. J. Clin. Invest. 96:2966–2974[Medline].
12. Barde, Y., Edgar, D., Thoenen, H. 1980. Sensory neurons in culture: changing requirements for survival factors during embryonic development. Proc. Natl. Acad. Sci. USA. 77:1199–1203[Medline].
13. Longo, F., Holtzman, D., Grimes, M., Mobley, W. 1992. Nerve growth factor: actions in the peripheral and central nervous systems. In Fallon J., Loughlin S., eds. Neurotrophic Factors. New York, Academic Press, 209–256.
14. Genain, C., Cannella, B., Hauser, S., Raine, C. 1999. Identification of autoantibodies associated with myelin damage in multiple sclerosis. Nat. Med. 5:170–175 [Medline].
15. Webster, H. D. 1997. Growth factors and myelin regeneration in multiple sclerosis. Mult. Scler. 3:113–120 [Medline].
16. Cannella, B., Hoban, C., Gao, Y., Garcia-Arenas, R., Lawson, D., Marchionni, M., Gwynne, D., Raine, C. 1998. The neuregulin, glial growth factor 2, diminishes autoimmune demyelination and enhances remyelination in a chronic relapsing model for multiple sclerosis. Proc. Natl. Acad. Sci. USA. 95:10100–10105[Medline].
17. Lovett-Racke, A., Bittner, P., Cross, A., Carlino, J., Racke, M. 1998. Regulation of experimental allergic encephalomyelitis with insulin growth factor (IGF-1) and IGF-1/IGF-binding protein-3 complex (IGF/IGFBP3). J. Clin. Invest. 101: 1797–1804[Abstract/Full Text].
18. Kramer, R., Zhang, Y., Gehrmann, J., Gold, R., Thoenen, H., Wekerle, H. 1995. Gene transfer through the blood-nerve barrier: NGF-engineered neuritogenic T lymphocytes attenuate experimental autoimmune neuritis. Nat. Med. 1:1162–1166[Medline].
19. Charlton, B., Lafferty, K. 1995. The Th1/Th2 balance in autoimmunity. Curr. Opin. Immunol. 7:793–798 [Medline].
20. Kossmann, T., Hans, V., Imhof, H., Trentz, O., Morgantikossmann, M. 1996. Interleukin-6 released in human cerebrospinal fluid following traumatic brain injury may trigger nerve growth factor production in astrocytes. Brain Res. 713:143–152[Medline].
21. De Simone, R., Micera, A., Tirassa, P., Aloe, L. 1996. mRNA for NGF and p75 in the central nervous system of rats affected by experimental allergic encephalomyelitis. Neuropathol. Appl. Neurobiol. 22:54–59[Medline].
22. Laudiero, L. B., Aloe, L., Levi-Montalcini, R., Buttinelli, C., Schilter, D., Gillessen, S., Otten, U. 1992. Multiple sclerosis patients express increased levels of beta-nerve growth factor in cerebrospinal fluid. Neurosci. Lett. 147:9–12[Medline].
23. Gadient, R. A., Cron, K. C., Otten, U. 1990. Interleukin-1 beta and tumor necrosis factor-alpha synergistically stimulate nerve growth factor (NGF) release from cultured rat astrocytes. Neurosci. Lett. 117:335–340[Medline].
24. Awatsuji, H., Furukawa, Y., Hirota, M., Murakami, Y., Nii, S., Furukawa, S., Hayashi, K. 1993. Interleukin-4 and -5 as modulators of nerve growth factor synthesis/secretion in astrocytes. J. Neurosci. Res. 34:539–545 [Medline].
25. Dugan, L. L., Creedon, D. J., Johnson, E. M., Jr., Holtzman, D. M. 1997. Rapid suppression of free radical formation by nerve growth factor involves the mitogen-activated protein kinase pathway. Proc. Natl. Acad. Sci. USA. 94:4086–4091 [Medline].
26. Fierz, W., Endler, B., Reske, K., Wekerle, H., Fontana, A. 1985. Astrocytes as antigen-presenting cells. I. Induction of Ia antigen expression on astrocytes by T cells via immune interferon and its effect on antigen presentation. J. Immunol. 134:3785–3793[Medline].
27. Williams, K., Dooley, N., Ulvestad, E., Becher, B., Antel, J. 1996. IL-10 production by adult human derived microglial cells. Neurochem. Int. 29:55–64[Medline].
28. Neumann, H., Misgeld, T., Matsumuro, K., Wekerle, H. 1998. Neurotrophins inhibit major histocompatibility class II inducibility of microglia: involvement of the p75 neurotrophin receptor. Proc. Natl. Acad. Sci. USA. 95:5779–5784[Medline].
29. Trapp, B., Peterson, J., Ransohoff, R., Rudick, R., Mork, S., Bo, L. 1998. Axonal transection in the lesions of multiple sclerosis. N. Engl. J. Med. 338:278–285 [Medline].
30. Steinman, L. 2000. Multiple approaches to multiple sclerosis. Nat. Med. 6:15–16
31. Villoslada et al. 2000 Human nerve growth factor protects common marmosets against autoimmune encephalomyelitis by switching the balance of T helper cell type 1 and 2 cytokines within the central nervous system. J. Exp. Med., 191(10): 1799–1806.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A process for suppressing the demyelination of nerve fibers in the nervous system of a human being or nonhuman primate in need of such treatment wherein said human being is treated with an amount of nerve growth factor (NGF) or with an amount of active fragments of NGF, which fragments are selected from the group consisting of NGF 2.5S, NGF 7S, and an NGF fragment consisting of oligopeptide of SEQ ID NO: 1 and the oligopeptide of SEQ ID NO: 2 linked by a disulfide bridge, which amount is effective to suppress demyelination.

2. The process according to claim 1, wherein said nerve growth factor is human NGF-β.

3. The process according to claim 1, comprising the administration of at least one protease inhibitor in combination with said NGF.

4. The process according to claim 3, wherein said protease inhibitor is aprotinin.

5. The method according to claim 1, wherein said NGF is a ministered in an amount sufficient to produce a concentration of NGF or an active fragment of NGF between 0.05 µg and 5 µg/kg body weight.

6. A process for suppressing further demyelination in the central nervous system of a human being or nonhuman primate having a disease in which a demyelination of nerve fibers occurs, comprising administering an amount of nerve growth factor or an amount of an active fragment thereof, which fragment is selected from the group consisting of NGF 2.5S, NGF 7S, and an NGF fragment consisting of SEQ ID NO:1 and the oligopeptide of SEQ ID NO:2 linked by a disulfide bridge, which amount is effective to prevent further demyelination.

7. The process according to claim 6, wherein the nerve growth factor is administered intravenously or intrathecally.

8. A method for suppressing further demyelination in the central nervous system of a human being or nonhuman primate having an inflammatory disease of the optic nerve, comprising administering an effective amount of NGF or an active fragment of NGF selected from the group consisting of NGF 2.5S and NGF 7S.

9. The method according to claim 8, wherein said effective amount of NGF or an active fragment of NGF is between 10–300 pg NGF/ml blood.

10. A method for suppressing demyelination in the central nervous system of the human being or nonhuman private having an inflammatory disease of a nervous tissue, said method comprising administering an effective amount of NGF, of an active fragment of NGF, which active fragment is selected from the group conisting of NGF 2.5S, and NGF fragment consisting of the oligopeptide of SEQ ID NO:1 and the oligopeptide of SEQ ID NO:2 linked by a disulfide bridge wherein said effective amount is sufficient to downregulate the production of interferon γ by T cells infiltrating the central nervous system.

11. The method of claim 10, wherein said effective amount is sufficient to upregulate the production of IL-10 in glial cells in the central nervous system.

12. The method of claim 10, wherein said inflammatory disease is autoimmune encephalomyelitis.

13. The method of claim 10, wherein said inflammatory disease is multiple sclerosis.

14. The method of claim 10, wherein said NGF is human NGF-β.

* * * * *